(12) United States Patent
Ibrahim et al.

(10) Patent No.: US 10,426,514 B2
(45) Date of Patent: Oct. 1, 2019

(54) SELF-DILATING CANNULA

(71) Applicant: LivaNova USA, Inc., Arvada, CO (US)

(72) Inventors: Tamer Ibrahim, Pleasant Hill, CA (US); Jeffrey P. Sites, West Chester, PA (US)

(73) Assignee: LivaNova USA, Inc., Arvada, CO (US)

( * ) Notice: Subject to any disclaimer, the term of this patent is extended or adjusted under 35 U.S.C. 154(b) by 271 days.

(21) Appl. No.: 15/133,106

(22) Filed: Apr. 19, 2016

(65) Prior Publication Data
US 2016/0228149 A1  Aug. 11, 2016

Related U.S. Application Data

(63) Continuation of application No. 12/973,741, filed on Dec. 20, 2010, now Pat. No. 9,339,599.
(Continued)

(51) Int. Cl.
*A61B 17/34* (2006.01)
*A61M 1/36* (2006.01)
(Continued)

(52) U.S. Cl.
CPC ....... *A61B 17/3431* (2013.01); *A61M 1/3653* (2013.01); *A61M 1/3659* (2014.02); *A61M 29/00* (2013.01); *A61B 2017/3456* (2013.01); *A61M 25/005* (2013.01); *A61M 25/007* (2013.01); *A61M 25/0041* (2013.01); *A61M 2025/0063* (2013.01)

(58) Field of Classification Search
CPC ................ A61M 1/3653; A61M 29/00; A61M 2025/0063; A61M 25/005; A61M 25/007; A61B 17/3431
See application file for complete search history.

(56) References Cited

U.S. PATENT DOCUMENTS

| 3,938,501 A | 2/1976 | Erikson |
| 4,129,129 A | 12/1978 | Amrine |

(Continued)

FOREIGN PATENT DOCUMENTS

| EP | 1704889 A1 | 9/2006 |
| WO | WO200004942 A1 | 2/2000 |

(Continued)

OTHER PUBLICATIONS

Extended European Search Report issued in 11850340.8, dated Apr. 4, 2014, 6 pages.
(Continued)

*Primary Examiner* — Bradley J Osinski
(74) *Attorney, Agent, or Firm* — Faegre Baker Daniels LLP

(57) ABSTRACT

A self-dilating cannula for introduction into a patient's vasculature includes an elongate body and an atraumatic tip. The elongate body has a proximal end, a distal end, and a fluid-flow lumen extending therebetween. The atraumatic tip is positioned at the elongate body's distal end and has a blunted end and a conical shape. The atraumatic tip includes a plurality of fluid-flow openings proximal to the blunted nose that are configured to disperse fluid from the fluid-flow lumen in a plurality of directions with respect to the atraumatic tip. The atraumatic tip also includes an opening in the blunted nose that is sized to a guidewire.

18 Claims, 3 Drawing Sheets

Related U.S. Application Data

(60) Provisional application No. 61/288,752, filed on Dec. 21, 2009.

(51) Int. Cl.
*A61M 29/00* (2006.01)
*A61M 25/00* (2006.01)

(56) References Cited

U.S. PATENT DOCUMENTS

| | | | |
|---|---|---|---|
| 4,180,068 | A | 12/1979 | Jacobsen et al. |
| 4,639,252 | A | 1/1987 | Kelly et al. |
| 4,808,158 | A | 2/1989 | Kreuzer et al. |
| 4,895,564 | A | 1/1990 | Farrell |
| 5,011,469 | A | 4/1991 | Buckberg et al. |
| 5,058,580 | A | 10/1991 | Hazard |
| 5,171,218 | A | 12/1992 | Fonger et al. |
| 5,190,528 | A | 3/1993 | Fonger et al. |
| 5,242,410 | A * | 9/1993 | Melker ............ A61M 25/06 604/164.1 |
| 5,308,325 | A | 5/1994 | Quinn et al. |
| 5,330,433 | A | 7/1994 | Fonger et al. |
| 5,354,276 | A | 10/1994 | Fonger et al. |
| 5,402,799 | A | 4/1995 | Colon et al. |
| 5,522,834 | A | 6/1996 | Fonger et al. |
| 5,584,803 | A | 12/1996 | Stevens et al. |
| D408,529 | S | 4/1999 | Hechel |
| 5,980,503 | A | 11/1999 | Chin |
| 6,090,072 | A | 7/2000 | Kratoska et al. |
| 6,126,594 | A | 10/2000 | Bayer |
| 6,186,981 | B1 | 2/2001 | Cho |
| 6,270,484 | B1 * | 8/2001 | Yoon ............ A61B 17/3494 604/264 |
| 6,488,693 | B2 | 12/2002 | Gannoe et al. |
| 6,497,698 | B1 | 12/2002 | Fonger et al. |
| 6,645,193 | B2 | 11/2003 | Mangosong |
| 6,676,650 | B1 | 1/2004 | Magovern et al. |
| 6,689,149 | B2 | 2/2004 | Maahs |
| 6,814,718 | B2 | 11/2004 | McGuckin, Jr. et al. |
| 6,837,864 | B1 | 1/2005 | Bertolero et al. |
| 6,902,545 | B2 | 6/2005 | Bertolero et al. |
| 6,951,555 | B1 | 10/2005 | Suresh et al. |
| 7,056,294 | B2 | 6/2006 | Khairkhahan et al. |
| D533,270 | S | 12/2006 | Kierce et al. |
| 7,267,660 | B2 | 9/2007 | Fonger et al. |
| 2002/0002376 | A1 | 1/2002 | Gannoe et al. |
| 2002/0022822 | A1 | 2/2002 | Cragg et al. |
| 2002/0049402 | A1 * | 4/2002 | Peacock, III .... A61B 17/00234 604/8 |
| 2002/0107506 | A1 * | 8/2002 | McGuckin, Jr. ...... A61M 1/285 604/523 |
| 2002/0133128 | A1 | 9/2002 | Heller |
| 2003/0216688 | A1 | 11/2003 | M.A.J.M. et al. |
| 2005/0085761 | A1 | 4/2005 | Wang et al. |
| 2005/0222532 | A1 | 10/2005 | Bertolero et al. |
| 2009/0182188 | A1 | 7/2009 | Marseille et al. |
| 2010/0049171 | A1 | 2/2010 | McQueen et al. |
| 2011/0004046 | A1 | 1/2011 | Campbell et al. |
| 2011/0152741 | A1 | 6/2011 | Banchieri et al. |
| 2011/0213316 | A1 | 9/2011 | Ibrahim et al. |
| 2012/0259273 | A1 | 10/2012 | Moshinsky et al. |

FOREIGN PATENT DOCUMENTS

| | | |
|---|---|---|
| WO | WO0134237 A1 | 5/2001 |
| WO | WO2003068303 A2 | 8/2003 |
| WO | WO2004037315 A2 | 5/2004 |
| WO | WO2005037345 A2 | 4/2005 |
| WO | WO2007052278 A2 | 5/2007 |
| WO | WO2008014792 A1 | 2/2008 |
| WO | WO2008065646 A1 | 6/2008 |

OTHER PUBLICATIONS

International Preliminary Report on Patentability, Chapter II, issued in PCT/AU2012/000347, completed Oct. 9, 2012, 15 pages.
International Preliminary Report on Patentability, Chapter II, issued in PCT/EP2012/060715, completed Aug. 19, 2013, 9 pages.
International Search Report and Written Opinion issued in PCT/AU2012/000347, dated May 22, 2012, 8 pages.
International Search Report and Written Opinion issued in PCT/EP2012/060715, dated Oct. 17, 2012, 11 pages.
International Search Report and Written Opinion issued in PCT/US2011/065820, dated Mar. 27, 2012, 12 pages.
Italian Search Report issued in Italian Application No. FI20110116, completed Jan. 27, 2012, 9 pages.
Magovern, James A. et al., "A Femoral Artery Cannula That Allows Distal Blood Flow"; The Journal of Thoracic and Cardiovascular Surgery, Sep. 2005; pp. 684-686.
Matsui et al.; "A Novel Femoral Arterial Cannula to Prevent limb Ischemia Durin~ Cardiopulmonary Support: Preliminary Report of Experimental and Clinical Experiences"; from Artif Organs, vol. 30, No. 7, 2006; 00.557-560.

* cited by examiner

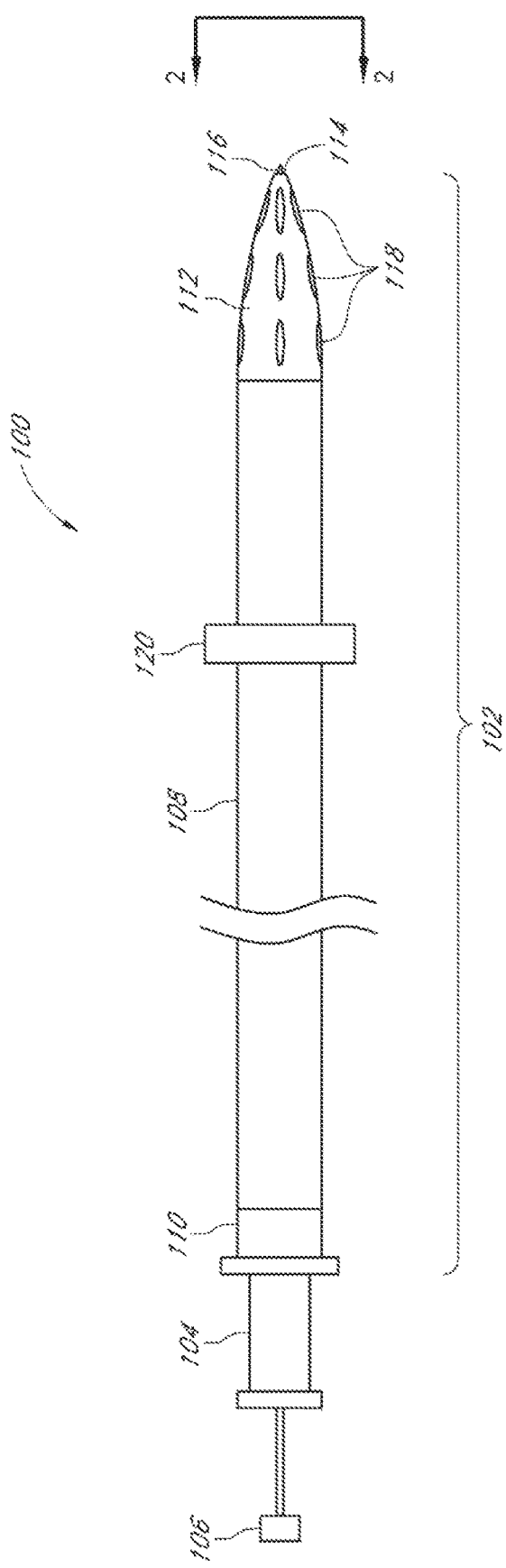
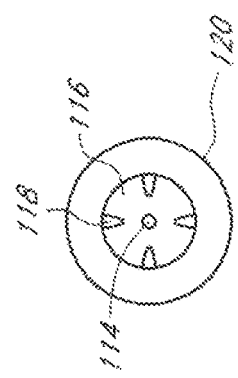
FIG. 1
FIG. 2

SELF-DILATING CANNULA

CROSS-REFERENCE TO RELATED APPLICATION

This application is a continuation of U.S. application Ser. No. 12/973,741, filed Dec. 20, 2010, which claims priority to U.S. Provisional Application No. 61/288,752, filed Dec. 21, 2009, all of which are herein incorporated by reference in their entirety.

This application is also related to U.S. Provisional Application Nos. 61/288,614 and 61/288,763, which are incorporated by reference in their entireties, herein.

SUMMARY

In one embodiment, a self-dilating cannula is configured for arterial perfusion or venous drainage. The cannula includes a conical tip that has a blunted nose, which provides self-dilation and minimizes the incision required for cannula introduction into a patient's vasculature. The canula's tip includes multiple ports that are configured to disperse fluid flow at a lower velocity in multiple directions. The cannula's tip also includes a small hole configured to be relatively conforming to a guidewire. The cannula is configured to receive the guidewire as the cannula is advanced through the patient's vasculature over the guidewire.

The cannula body includes an obturator, which can extend through the cannula's tip, or terminate within the cannula's body. The obturator includes a central lumen configured to receive a stylet. The stylet allows the cannula and obturator to be pre-shaped, or given a predetermined shape, which provides simplified remote insertion. The stylet also provides additional column strength to the cannula-obturator assembly. The stylet can include a sharpened incising distal tip to facilitate insertion of the cannula assembly into the patient's vasculature.

The cannula body can be thick- or thin-walled. In a thin wall configuration, the cannula body can include a reinforcing element to provide additional column strength. For example, in one embodiment, the cannula body includes a wound wire, spring, or discrete sections of material that are stiffer than the overlying cannula material.

In one embodiment, the cannula also includes an external concentric stop which limits the distance the tip of the cannula can be inserted in the patient's vasculature. The cannula may be used in a variety of applications, and at a variety of insertion sites, including the aorta, axillary vessels, femoral vessels, superior vena cava, and/or right atrium of the patient's heart.

BRIEF DESCRIPTION OF THE DRAWINGS

FIG. 1 illustrates a side view of a self-dilating cannula assembly, in accordance with one embodiment;

FIG. 2 illustrates a distal end view observed along line 2-2 of the cannula assembly of FIG. 1;

DETAILED DESCRIPTION

Figure 3:
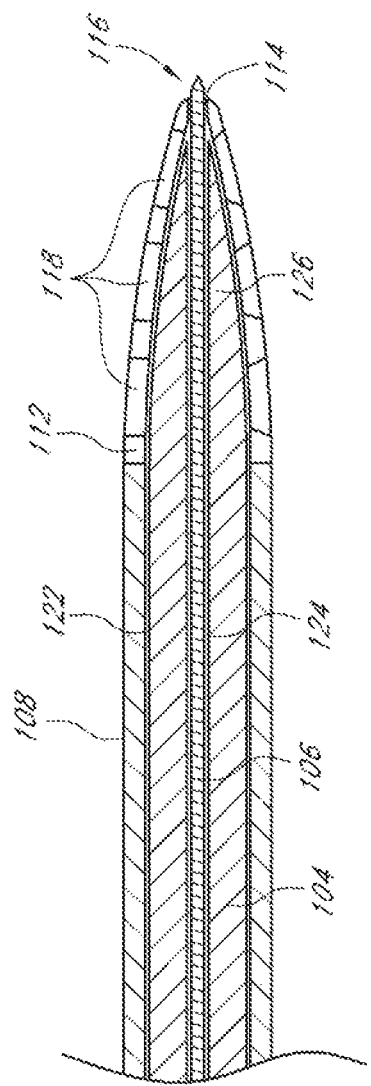
FIG. 3 illustrates a partial cross-sectional view of the cannula assembly of FIG. 1.

FIG. 1 illustrates one embodiment of a self-dilating cannula assembly 100. The cannula assembly 100 includes a cannula 102, obturator 104, and stylet 106. The cannula 102 includes a tubular, elongate body 108 that terminates at a connector 110 at the elongate body's proximal end and at a cannula tip 112 at the elongate body's distal end. An opening 114 located at the tip's distal end is sized to receive a piercing tip 116 of the stylet 106. The cannula tip 112 includes ports 118 configured to permit adequate fluid flow through the cannula 102 and to, or from, a patient's vasculature. An optional stop 120 allows a clinician to control the degree of insertion of the distal end of the cannula 102 into a patient's vasculature. The stop 120 is slideable along the elongate body 108, but is held in position with a locking mechanism. In one embodiment, the locking mechanism includes a friction grip between the stop 120 and the elongate body 108.

The cannula tip 112 can have a conical shape and/or a blunted and/or rounded nose. The taper and curvature of the tip 112 is selected to provide self-dilation of an opening at an insertion site as the cannula 102 is advanced through the opening. The cannula tip's shape also minimizes the incision required to insert the cannula 102 into the patient's vasculature. In one embodiment, the diameter of the distal end of the cannula tip 112 is about 0.04", 0.06", or 0.10".

The ports 118 are configured to disperse fluid flow at low velocity in multiple directions. For example, in one embodiment, ports 118 are longitudinally and/or circumferentially spaced along the tip's 112 wall. The opening 114 at the cannula tip's distal end is configured to conform to a guidewire and/or stylet.

In one embodiment, the obturator 104 extends through the elongate body 108 and into the cannula tip 112. In another embodiment, the obturator 104 extends only through the elongate body 108 and terminates within it. The obturator 104 is designed to accept a sytlet 106. The stylet 106 may be used to shape and/or apply a predetermined curvature to the cannula 102 prior to insertion into the patient's vasculature. In some cases, shaping the cannula 102 by bending the stylet 106 simplifies the procedure of inserting the cannula 102 into the patient's vasculature. Furthermore, the stylet 106 also provides additional column strength to the cannula 102, which further simplifies insertion. In one embodiment, the stylet 106 has an outer diameter of about 0.038".

The tissue-piercing tip 116 of the stylet 106 greatly simplifies the cannula-insertion process by acting as a leading-edge cutter. For example, the self-dilating cannula system 100 allows a clinician to position the cannula 102 with respect to a tissue insertion site, and with a single motion, pierce the tissue wall at the insertion site, insert and advance the cannula 102 into the patient's vasculature. The clinician may avoid the time-consuming procedures of incising the tissue wall at an insertion site, clamping the incision to stop blood flow, and utilizing a separate set of dilators to expand the incision at the insertion site, as well as the vessel lumen, in order to accept a cannula. Instead, the self-dilating cannula system 100 may be introduced into the patient's vasculature quickly, safely, and under direct vision.

The elongate body 108 can include a thick- or thin-wall configuration. For example, the elongate body 108 can have a wall thickness in the range of about 0.020"-0.080", 0.040"-0.060", or about 0.050". The elongate body 108 wall can optionally include a reinforcing element (not shown). For example, in some embodiments, the elongate body 108 wall includes a wire, a wound wire, a spring, or areas or sections of material having increased stiffness compared to other areas or sections of materials.

FIG. 2 illustrates the distal end view of the cannula assembly 100 observed along line 2-2 of FIG. 1. Several ports 118 located on the cannula tip 112 are sized and oriented to allow blood to smoothly flow along the direction of a longitudinal axis of the elongate body 108. Such ports 118 allow fluid to flow through and exit (or enter) the cannula 102 via ports 118 in the cannula tip 112 that open along the elongate body's longitudinal axis.

FIG. 3 illustrates a partial cross-sectional view of the cannula assembly 100 of FIG. 1. The cannula's elongate body 108 includes an elongate body lumen 112, which is sized to receive the obturator 104. The elongate body lumen 122 diameter is slightly larger than the outside diameter of the obturator 104 so that the obturator can freely slide in and out of elongate body 108, as desired. The obturator 104 includes an obturator lumen 124, which is sized to receive the stylet 106. Similarly, the obturator lumen 124 diameter is slightly larger than the outside diameter of the stylet 106 so that the stylet can freely slide in and out of the obturator, as desired.

The degree or amount of obturator 104 insertion into the elongate body 108 may be controlled by an interference between the distal end 126 of the obturator 104 and the inside surface of the cannula tip 112. In another embodiment, the amount of obturator 104 insertion into the elongate body 108 is controlled by a limit (not shown) positioned near the proximal end of the obturator 104. The limit is designed to interfere with (e.g., contact) the connector 110 located at the elongate body's 108 proximal end.

Similarly, the degree or amount of stylet 106 insertion into the obturator 104 may be controlled by an interference between the distal end of the stylet 106 and the inside surface of the obturator's 104 distal end. In another embodiment, the amount of stylet 106 insertion into the obturator 104 is controlled by a limit (not shown) positioned near the proximal end of the stylet. The limit is designed to interfere with (e.g., contact) an end portion located at the obturator's 104 proximal end.

Figure 4:
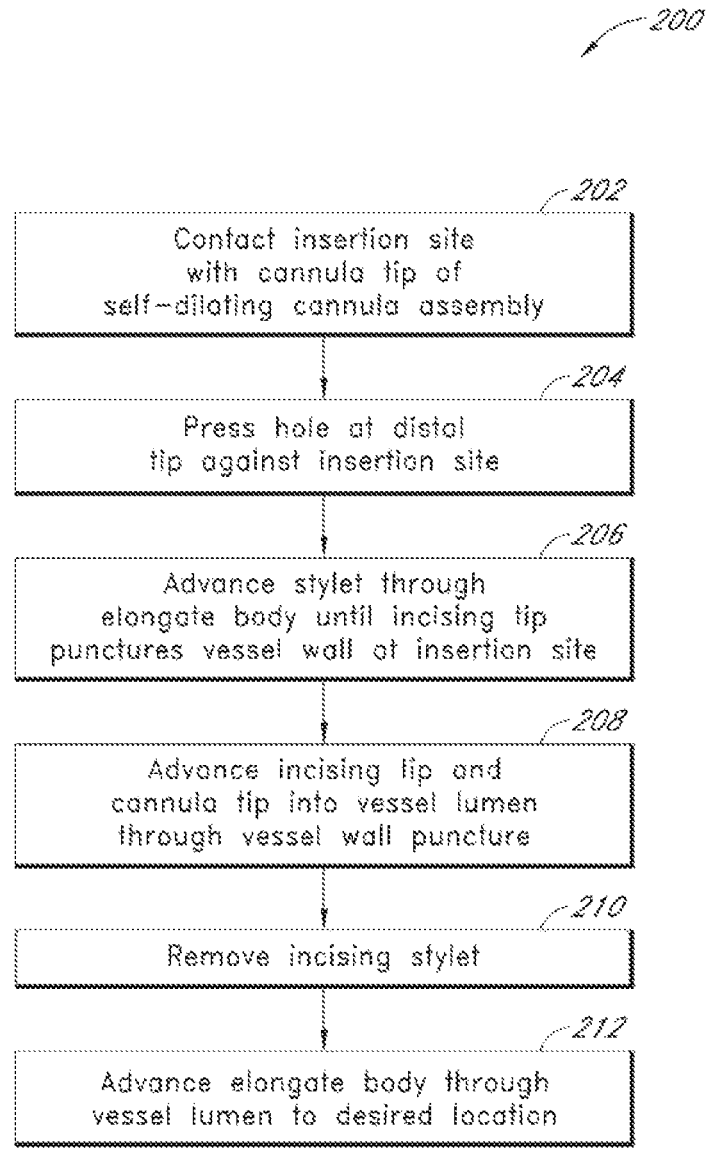
FIG. 4 illustrates a flow chart of one embodiment of a method of inserting a cannula into a bodily lumen.

FIG. 4 illustrates a method 200 of inserting a cannula into a bodily lumen of a medical patient. The cannula utilized to perform the method 200 can be any of the cannulae described above, including, but not limited to the cannula assembly 100 of FIGS. 1-3. In other embodiments, a different cannula is utilized.

The method 200 begins at block 202, where an insertion site is contacted with a cannula tip of a self-dilating cannula. At block 204, a hole located at the distal end of the distal tip is pressed against the insertion site. An obturator may be inserted into the cannula to provide column strength and additional stiffness and control over the cannula. At block 206, a stylet is advanced through the elongate body of the cannula until the stylet's incising tip exits the cannula hole and punctures the tissue at the insertion site. The tissue can include one or more of skin, muscle, fat, and a vessel wall, such as a blood vessel, artery, vein, or other bodily conduit. The incising tip of the stylet punctures the tissue at the insertion site while the distal end of the cannula tip is held in contact with the vessel wall around the insertion site.

At bock 208, the incising tip and cannula tip are initially advanced into the vessel lumen through the vessel wall puncture. The incising stylet is removed from the patient's vasculature and the obturator lumen at block 210. The incising stylet is removed to reduce the risk of undesired damage to the luminal wall of the patient's vessel. At block 212, the elongate body is further advanced through the vessel lumen. If a stop is provided, the cannula is advanced until the stop contacts tissue around the insertion site.

In one embodiment, the cannula is inserted into the patient's vasculature over a guidewire. For example, after the incising stylet is removed, a guidewire is inserted through the obturator lumen in which the stylet had been inserted prior to removal. The guidewire is advanced through the obturator lumen until it exits the hole at the cannula's distal tip, and then enters the patient's vasculature through the puncture at the insertion site. The cannula slides over the guidewire and follows the guidewire through the patient's vasculature as it is advanced.

The self-dilating cannula system can be used in any of a variety of clinical applications. For example, the cannula system can be inserted into any blood-carrying vessel, chamber, or volume within a patient, including, but not limited to, the aortic artery, the axillary artery, the femoral artery, the subclavian artery, the inferior vena cava, the superior vena cava, and/or a chamber of the heart, including the right or left atrium or the right or left ventricle.

The self-dilating cannula can be used for arterial perfusion and/or venous drainage. For example, once introduced into a patient's aortic artery (as described above), the stylet and obturator are removed from the cannula. The connector at the cannula's proximal end may then be connected to the output port of a cardio-pulmonary bypass pump, such that externally oxygenated blood from the cardio-pulmonary bypass pump is introduced into the patient's aorta via the cannula. The self-dilating cannula can be guided percutaneously to the appropriate position within the person's aorta by using a guidewire. Alternatively, the self-dilating cannula can be directly inserted into the patient's aorta by least-invasive, port, or open chest surgical techniques.

In another embodiment, the self-dilating cannula is used to retrieve deoxygenated blood from the patient's vasculature. For example, the self-dilating cannula may be advanced percutaneously through the patient's femoral artery, to the inferior or superior vena cava. The connector at the cannula's proximal end may then be connect to the input port of a cardio-pulmonary bypass pump, such that deoxygenated blood retrieved from the patient is externally reoxygenated and then reintroduced into the patient's vasculature. In one embodiment, two self-dilating cannulae are provided. For example, a first cannula is coupled between the patient's venous system (e.g., superior and/or inferior vena cava) and a cardio-pulmonary bypass pump, and a second cannula is coupled between the cardio-pulmonary bypass pump and the patient's arterial system (e.g., aorta).

In certain embodiments, features of the cannulae and related methods described above are applied to, or use in accordance with any one or more of the devices and methods described in U.S. Pat. Nos. 6,837,864 and 6,902,545, which are incorporated by reference in their entireties herein.

We claim:

1. A cannula assembly comprising:
   a cannula comprising:
     an elongate body having a proximal end, a distal end, and a fluid-flow lumen extending therebetween; and
     an atraumatic tip positioned at the elongate body's distal end;
   a stylet having a stylet distal end; and
   an obturator comprising a lumen sized to receive the stylet, wherein the obturator is sized to provide an interference fit between the stylet distal end of the stylet and an inside surface of a distal end of the obturator, wherein the interference fit is configured to control an amount of stylet insertion into the obturator.

2. The cannula assembly of claim 1, wherein the atraumatic tip includes a blunted nose and a conical portion, wherein the blunted nose includes an opening.

3. The cannula assembly of claim 2, wherein the atraumatic tip includes a plurality of fluid-flow openings on the conical portion of the atraumatic tip.

4. The cannula assembly of claim 3, wherein the fluid-flow openings are sized and oriented to allow blood to flow along a direction of a longitudinal axis of the elongate body.

5. The cannula assembly of claim 1, wherein the stylet is configured to provide a predetermined shape to the elongate body when inserted therein.

6. The cannula assembly of claim 1, wherein the elongate body further includes at least one reinforcing element configured to provide increased stiffness to the elongate body.

7. The cannula assembly of claim 6, wherein the at least one reinforcing element includes at least one of: a wire and a spring.

8. The cannula assembly of claim 1, further comprising an external stop disposed concentrically around the elongate body, the stop being slideable along the elongate body and configured to control a degree of insertion of the distal end of the cannula into a patient's vasculature.

9. The cannula assembly of claim 8, the stop including a locking mechanism configured to hold the stop in place at a position on the elongate body.

10. The cannula assembly of claim 1, further comprising an external stop disposed concentrically around the elongate body, the stop being slideable along the elongate body and configured to control a degree of insertion of the distal end of the cannula into a patient's vasculature, wherein the stop includes a locking mechanism configured to hold the stop in place on the elongate body.

11. A cannula assembly comprising:
a cannula comprising:
an elongate body having a proximal end, a distal end, and a fluid flow lumen extending therebetween; and
an atraumatic tip positioned at the elongate body's distal end;
a stylet having a predetermined shape; and
an obturator comprising a lumen sized to receive the stylet, wherein the obturator is sized to be inserted into the fluid flow lumen and wherein an inside surface of the obturator lumen is sized to receive the stylet and the stylet provides the predetermined shape to the elongate body when inserted therein, wherein the obturator is sized to provide an interference fit between a distal end of the stylet and an inside surface of a distal end of the obturator.

12. The cannula assembly of claim 11, wherein the atraumatic tip includes a blunted nose and a conical portion, wherein the blunted nose includes an opening and wherein the opening has a diameter that is less than 6% greater than the diameter of the stylet.

13. The cannula assembly of claim 12, wherein the atraumatic tip includes a plurality of fluid-flow openings on the conical portion of the atraumatic tip.

14. The cannula assembly of claim 13, wherein the fluid-flow openings are sized and oriented to allow blood to flow along a direction of a longitudinal axis of the elongate body.

15. The cannula assembly of claim 11, wherein the elongate body further includes at least one reinforcing element configured to provide increased stiffness to the elongate body.

16. The cannula assembly of claim 15, wherein the at least one reinforcing element includes at least one of: a wire and a spring.

17. A method for inserting a cannula comprising
providing a cannula assembly, the cannula assembly comprising:
a cannula comprising:
an elongate body having a proximal end, a distal end, and a fluid-flow lumen extending therebetween; and
an atraumatic tip positioned at the elongate body's distal end; and
an obturator comprising a lumen sized to receive a stylet, wherein the obturator is sized to provide an interference fit, at an interference point, between a distal end of the stylet and an inside surface of a distal end of the obturator, wherein the interference fit is configured to control an amount of stylet insertion into the obturator;
contacting an insertion site with the atraumatic tip;
advancing a stylet through the obturator lumen to the interference point, wherein the obturator interferes with the stylet advancing further at the interference point and wherein the stylet punctures a vessel wall of a blood vessel at the interference point;
removing the stylet; and
advancing the elongate body through the puncture in the vessel wall to an insertion point.

18. The method of claim 17, wherein the cannula assembly includes an external stop disposed concentrically around the elongate body and wherein advancing the elongate body through the puncture in the vessel wall to the insertion point comprises advancing the cannula assembly until the stop contacts the insertion site.

* * * * *